United States Patent
Nestler

[11] Patent Number: 6,063,753
[45] Date of Patent: May 16, 2000

[54] SURFACTANT MIXTURES COMPRISING ACYLOXYALKANESULFONATES

[75] Inventor: Bernd Nestler, Frankfurt, Germany

[73] Assignee: Clariant GmbH, Frankfurt, Germany

[21] Appl. No.: 08/936,390

[22] Filed: Sep. 25, 1997

[30] Foreign Application Priority Data

Oct. 1, 1996 [DE] Germany .......................... 196 40 572

[51] Int. Cl.⁷ .................. C11D 9/00; A61K 7/50
[52] U.S. Cl. .................. 510/495; 510/156; 510/492; 510/493; 510/536
[58] Field of Search .................. 510/156, 492, 510/493, 495, 536; 558/44

[56] References Cited

U.S. PATENT DOCUMENTS

| | | | |
|---|---|---|---|
| 3,029,264 | 4/1962 | Alphen et al. | |
| 4,231,904 | 11/1980 | Machin | 510/155 |
| 4,696,767 | 9/1987 | Novakovic et al. | 510/536 |
| 4,790,956 | 12/1988 | Weipert et al. | 510/537 |
| 5,384,421 | 1/1995 | Day et al. | |

FOREIGN PATENT DOCUMENTS

| | | |
|---|---|---|
| 4236502 | 5/1994 | Germany . |
| WO 94/09107 | 4/1994 | WIPO . |
| WO 95/11957 | 5/1995 | WIPO . |

*Primary Examiner*—Necholus Ogden
*Attorney, Agent, or Firm*—Miles B. Dearth

[57] ABSTRACT

Surfactant mixtures based on acyloxyalkanesulfonates prepared by reacting more than one mole of one or more fatty acids with one mole of a mixture of alkali metal and/or alkanline earth metal hydroxyalkanesulfonate and ammonium hydroxyalkanesulfonate in the presence of an esterification catalyst at a temperature from 100 to 260° C.

6 Claims, No Drawings

SURFACTANT MIXTURES COMPRISING ACYLOXYALKANESULFONATES

BACKGROUND OF THE INVENTION

Acyloxyalkanesulfonates are anionic surfactants used as base materials for syndet soaps, cosmetic compositions and cleaning formulations. Their features include good foaming properties, good hard water stability and good skin compatibility.

Disadvantages of the use of these surfactants are that the majority of them are brittle solids which are stirrable or melt only at high temperatures. At these high temperatures required just to make it possible to process the acyloxyalkanesulfonate the latter is highly sensitive to oxidation; thermal decomposition begins, and discoloration occurs.

Accordingly, it is advantageous to lower the melting point or the temperature at which the acyloxyalkanesulfonates are stirrable and can thus be processed. To solve this problem it has already been disclosed to prepare acyloxyalkanesulfonates of this type comprising mixed salts, i.e. where the cation consists of a mixture of two different cations, for example sodium and potassium ion (U.S. Pat. No. 3,029,264). These acyloxyalkanesulfonates, which are preferably acyloxyisethionates, are prepared by esterifying fatty acids with a salt of isethionic acid. If, then, in accordance with the details of this prior art, a mixture of Na isethionate and K isethionate is employed, the esterification with the fatty acid can be conducted at just 150 to 160° C. This makes it possible to avoid the development of discoloration. With this process, however, equimolar amounts of fatty acid and isethionate are reacted in every case. It has now been found that in the case of such acyloxyalkanesulfonates having mixed cations it is possible to reduce still further the stirrability limit, i.e. the temperature at which the product can still just be stirred, if rather than equimolar amounts an excess of fatty acid is employed.

Acyloxyalkanesulfonates with mixed cations have also been described in WO 94/09107. In that document, however, there is no indication as to the effects of the mixed cations on the preparation conditions.

SUMMARY OF THE INVENTION

The invention provides surfactant mixtures based on acyloxyalkanesulfonates prepared by reacting more than one mole of one or more fatty acids with one mole of a mixture of alkali metal and/or alkaline earth metal hydroxyalkanesulfonate and ammonium hydroxyalkanesulfonate in the presence of an esterification catalyst at a temperature from 150 to 200° C.

Suitable fatty acids are saturated or unsaturated fatty acids containing 8 to 32 C atoms. Examples are caproic acid, capric acid, lauric acid, myristic acid, stearic acid, arachidic acid, oleic acid, linoleic acid and linolenic acid. Preference is given to mixtures of fatty acids, for example coconut fatty acid and tallow fatty acid. Not only unbranched but also branched fatty acids are suitable, for example 2-ethylhexanoic acid, 2-pentyloctanoic acid, 2-butyinonanoic acid, 2-propyldecanoic acid, 2-ethylundecanoic acid, 2-butylundecanoic acid, 2-methyidodecanoic acid, 2-ethyltridecanoic acid and 2-methyltetradecanoic acid, and mixtures thereof.

DESCRIPTION OF THE PREFERRED EMBODIMENTS

The hydroxyalkanesulfonates are of the formula HO—$R^1$—$SO_3$X in which $R^1$ is —$CH_2CH_2$—, —$(CH_2)_3$—, —$CH_2CH(CH_3)$— or —$CH_2CH_2OCH_2CH_2$—, preferably ethylene. X herein denotes an equivalent amount of a mixture of alkali metal and/or alkaline earth metal cations, preferably sodium or potassium and ammonium cations. The ammonium cations have the formula

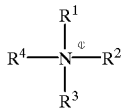

in which $R^1$, $R^2$, $R^3$ and $R^4$ can be identical or different and are hydrogen or $C_1$–$C_4$-alkyl, preferably methyl or ethyl, or $C_1$–$C_4$-hydroxyalkyl, $R^1$ to $R^4$ being identical or different. Preference is given to sodium, potassium, $^+NH(CH_3)_3$, $^\oplus NH(C_2H_5)_3$, $HN^\oplus(CH_2CH_2OH)_3$ and $NH^\oplus_4$ cations. The proportion of the individual cations can vary within wide limits; what is important in each case is that X in the above formula is not a single cation but a mixture of different cations. Part of this mixture of the different cations is in every case any desired ammonium cation of the abovementioned formula, with the remainder then being, for example, a sodium or potassium ion. Also possible are mixtures of three or more different cations, for example mixtures of sodium, potassium and ammonium ions.

Preference is given to novel surfactant mixtures which are prepared such that in said mixtures the acyloxyalkanesulfonates feature the following molar ratios of the cations: K:$NH_4$ from 97:3 to 5:95; Na:$NH_4$ from 98:2 to 5:95, especially 97:3 to 50:50;
Na:$NH(C_2H_5)_3$ from 98:2 to 10:90; K:$NH(C_2H)_3$ from 98:2 to 10:90.

The novel surfactant mixtures are preferably prepared by the process of so-called direct esterification, by reacting an excess of fatty acid with the hydroxyalkane-sulfonate in the presence of an esterification catalyst at a temperature from 100 to 260° C. with simultaneous removal of the water present. This direct esterification is carried out in detail in analogy to the indications in EP-A-0 585 071 (U.S. Pat. No. 5,384,421), which is incorporated herein by reference.

In preparing the novel surfactant mixtures it is critical to employ a molar excess of fatty acid based on hydroxyalkanesulfonate. An excess of up to 2 mol of fatty acid per mole of hydroxyalkanesulfonate is preferred.

The salts of the hydroxyalkanesulfonic acid can be employed as such but are preferably employed in the form of an aqueous solution, generally as a from 40 to 65% strength by weight solution.

Appropriate esterification catalysts have been described at length in the abovementioned EP-A-0 585 071, incorporated herein by reference. They comprise alkanesulfonic acids, hydroxyalkanesulfonic acids, arylsulfonic acids, inorganic acids such as sulfuric acid, phosphoric acid, phosphorous acid, boric acid or their anhydrides, heavy metal salts such as zinc sulfate, zirconium sulfate, zinc isethionate, zinc borate, aluminum sulfate, titanium sulfate or tungsten phosphate, metal oxides such as zinc oxide, aluminum oxide, magnesium oxide, cerium oxide, zirconium oxide or lanthanum oxide, and also mixtures of two or more of these catalysts, and soaps formed from heavy metals and metal oxides. A particularly preferred esterification catalyst is zinc oxide. The esterification catalyst is employed in an amount of in general from 0.05 to 2% by weight, preferably from 0.05 to 1% by weight, based on hydroxyalkanesulfonate.

In detail, the esterification can be conducted by charging the fatty acid, the hydroxyalkanesulfonate and the esterification catalyst under atmospheric pressure to a reaction vessel and heating the mixture to the temperature indicated above with stirring. Both the water which may be introduced into the reaction mixture together with the starting components and the water which is formed as a result of the esterification reaction are discharged continuously from the reaction mixture during this process. In addition, it may also be sensible to distil off some of the excess fatty acid in the course of the esterification reaction.

The esterification reaction can also be commenced at atmospheric pressure and then subjected to reduced pressure in order to discharge the water more rapidly. The time for the desired degree of conversion of fatty acid or of ammonium hydroxyalkanesulfonate to be reached is from about 4 to 8 hours. In general, for reasons of time, for example, the target conversion will be not 100% but instead a lower percentage, for example from 75 to 90% by weight, of acyloxyalkanesulfonate, at which point the esterification reaction will be brought to an early close, for example by cooling. The reaction product obtained is solid or liquid at room temperature. A product which is solid at room temperature can be worked up, for example, with the aid of a flaking roll or a cooling belt.

In order to reduce the viscosity of the reaction mixture it is possible to add so-called consistency regulators to it before or during the cooling operation. Examples of suitable such regulators are paraffins, as described in EP-A-0 585 071, fatty acids, fatty acid esters, polyethylene glycols or mixtures of consistency regulators. Preference is given to free fatty acids, especially those whose chain length differs from that of the fatty acid used to prepare the acyloxyalkanesulfonate. The proportion of these consistency regulators can be up to 60% by weight, preferably up to 30% by weight. Preference is given to mixtures comprising up to 30% by weight of paraffin, up to 50% by weight of fatty acid and up to 10% by weight of polyethylene glycol. The percentages are based in each case on the content of the material comprising the acyloxyalkanesulfonate.

The surfactant mixtures prepared in the manner described, which as principal component comprise acyloxyalkanesulfonates with mixed cations, along with residual amounts of free fatty acids and, if used, consistency regulator, have the distinction over similar products of the prior art (U.S. Pat. No. 3,029,264) that for a given content of acyloxyalkanesulfonate the temperature limit at which the surfactant mixture is still stirrable is markedly lower. This reduction in the stirrability limit with the novel surfactant mixtures means that in this case the content of acyloxyalkanesulfonate can be higher than in the mixtures of said prior art. A further reduction in the stirrability limit may take place through the addition of consistency regulators. Moreover, with the novel surfactant mixtures the residual content of free isethionate is significantly lower.

EXAMPLES

Examples 1 to 7

230 g of coconut fatty acid (1.12 mol), the amounts of aqueous Na isethionate and NH$_4$ isethionate solution corresponding to a total amount of 1.0 mol, and 0.71 g of zinc oxide were charged to a 2 l beaker with ground glass joints fitted with stirrer, descending distillation bridge, internal thermometer and nitrogen inlet. The reaction mixture was heated to 220° C. and the water formed in the direct condensation was removed by distillation. At a content of acylisethionate (wash-active substance—WAS) of about 80% (Epton titration) the reaction mixture was slowly cooled with stirring and the stirrability limit, i.e. the temperature at which the mixture is still stirrable, the WAS content, and the content of free hydroxyethanesulfonate anion were measured. The results obtained were as follows:

| Ex. No. | Proportion Na/ NH$_4$ isethionate Na | NH$_4$ | stirrable to [° C.] | WAS [%] | Hydroxyethanesulfonate anion [% by wt.] |
|---|---|---|---|---|---|
| 1 | 100 | 0 | 195 | 81 | 4.2 |
| 2 | 95 | 5 | 95 | 80 | 4.3 |
| 3 | 90 | 10 | 105 | 79 | 4.3 |
| 4 | 85 | 15 | 170 | 80 | 4.1 |
| 5 | 70 | 30 | 180 | 80 | 3.5 |
| 6 | 30 | 70 | 175 | 79 | 2.2 |
| 7 | 0 | 100 | 180 | 81 | 3.3 |

Examples 8 to 14

In accordance with the previous examples, acylisethionate melts were prepared into each of which 62 g of stearic acid as consistency regulator were additionally stirred. The formulations were then cooled and the stirrability limit, the WAS content and the content of free hydroxyethanesulfonate anion in the end product were measured. The results are summarized in the following table:

| Ex. No. | Proportion Na/ NH$_4$ isethionate Na | NH$_4$ | stirrable to [° C.] | WAS [%] | Hydroxyethanesulfonate anion [% by wt.] |
|---|---|---|---|---|---|
| 8 | 100 | 0 | 150 | 67 | 3.6 |
| 9 | 95 | 5 | 78 | 73 | 3.7 |
| 10 | 90 | 10 | 70 | 69 | 3.7 |
| 11 | 85 | 15 | 92 | 68 | 3.5 |
| 12 | 70 | 30 | 105 | 68 | 3.0 |
| 13 | 30 | 70 | 110 | 68 | 1.9 |
| 14 | 0 | 100 | 140 | 69 | 2.8 |

Example 15

In accordance with Examples 6–12, 224 g of lauric acid, 76.6 g of aqueous sodium isethionate solution (58%), 181 g of aqueous ammonium isethionate solution (55%) and 0.71 g of zinc oxide were initially taken and the reaction mixture was condensed at 180° C. At a WAS content of 81% (Epton titration) the mixture was no longer stirrable, and the content of free hydroxyethanesulfonate anion was 2.2%.

Addition of 62 g of stearic acid made it possible to reduce the stirrability limit to 130° C.; the resulting product had a content of wash-active substance of 70% (Epton titration) and a content of free hydroxyethanesulfonate of 1.9%.

Examples 16 to 18

283 g of coconut fatty acid, 243 g of aqueous sodium isethionate solution (58%) and 13.5 g of aqueous ammonium isethionate solution (53%) were charged to a 3 l beaker with ground glass joints fitted with stirrer, descending distillation bridge, internal thermometer and nitrogen inlet, and the reaction mixture was condensed at 180° C. to a content of wash-active substance of 77%, during which the water formed in the reaction was removed by distillation. Following the addition of appropriate additives (see table) the WAS contents and stirrability limits of the resulting sodium/ ammonium cocoylisethionate melts were measured.

| Experiment No. | Additives | stirrable to [° C.] | WAS [%] |
|---|---|---|---|
| 16 | 158 g of paraffin | 60 | 56 |
| 17 | 158 g of stearic acid | 65 | 56 |
| 18 | 48.3 g of paraffin<br>58.5 g of stearic acid<br>25.6 g of lauric acid<br>25.6 g of polyethylene glycol | 45 | 56 |

Example 19

308 g of coconut fatty acid, 253 g of aqueous sodium isethionate solution (58%), 141 g of aqueous potassium isethionate solution (53%) and 16.2 g of aqueous ammonium isethionate solution (53%) and 1.1 g of zinc oxide were charged to a beaker with ground glass joints fitted with stirrer, descending distillation bridge, internal thermometer and nitrogen inlet. The reaction mixture was heated to 220° C., and the water formed in the course of the direct condensation was removed by distillation. At a content of wash-active substance (WAS) of 84% (Epton titration) the reaction mixture was cooled slowly with stirring. The resulting sodium/potassium/ammonium cocoylisethionate mixture was stirrable up to a temperature of 145° C.

Example 20

In accordance with the preceding example, a sodium/potassium/ammonium cocoyisethionate melt was prepared. After mixing in 99 g of stearic acid the melt was slowly cooled; at a WAS content of 69% the stirrability limit was 105° C.

Example 21 (corresponding to Example 5 of U.S. Pat. No. 3,029,264)

In analogy to Example 15, 200 g of lauric acid, 44.4 g of sodium isethionate, 100 g of ammonium isethionate and 3.5 g of toluenesulfonic acid were reacted at 120–125° C. At a WAS content of just 55% (Epton titration) the mixture could no longer be stirred. Only by raising the reaction temperature to 180° C. was it possible to continue the condensation. The resulting product, which at this temperature was no longer stirrable, had a WAS content of 77% (Epton titration) and a content of free hydroxyethanesulfonate anion of 7.8%.

As evident from comparing the two Examples 15 and 21, a surfactant mixture obtained in the novel manner, i.e. with a molar excess of fatty acid, has a WAS content at the stirrability limit which is markedly higher than in the case of the prior art product. Moreover, it was possible in accordance with the invention to bring about a significant reduction in the content of free hydroxyalkanesulfonate.

I claim:

1. A surfactant mixture based on acyloxyalkanesulfonates prepared by reacting more than one mole of one or more fatty acids with one mole of a mixture of (a) and (b), wherein
   (a) is an alkali metal and/or alkaline earth metal hydroxyalkanesulfonate and
   (b) is an ammonium hydroxyalkanesulfonate said (a), (b) and said one or more fatty acids reacted in the presence of an esterification catalyst at a temperature from 100 to 260° C. wherein said surfactant mixture resulting therefrom contains ammonium cations and alkali metal and/or alkaline earth metal cations having a molar ratio of alkali and/or alkaline earth metal to ammonium cations of from 98:2 to 5:95, respectively, to reduce the stirribility limit.

2. The surfactant mixture as claimed in claim 1, wherein the acyloxyalkanesulfonate is an acylisethionate.

3. The surfactant mixture as claimed in claim 1, wherein the alkali metal and/or alkaline earth metal hydroxyalkanesulfonate is a sodium and/or potassium hydroxyalkanesulfonate.

4. The surfactant mixture as claimed in claim 1, wherein the ammonium cation of the hydroxyalkanesulfonate is of the formula

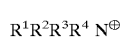

in which $R^1$, $R^2$, $R^3$ and $R^4$ are hydrogen, $C_1$–$C_4$-alkyl or $C_1$–$C_4$-hydroxyalkyl.

5. The surfactant mixture as claimed in claim 1, prepared by reaction of coconut fatty acid.

6. The surfactant mixture as claimed in claim 1, wherein the acyloxyalkanesulfonate is present as a mixed sodium and ammonium salt with a molar ratio of Na to $NH_4$ of from 98:2 to 5:95.

* * * * *